(12) United States Patent
Coffin et al.

(10) Patent No.: US 9,475,854 B2
(45) Date of Patent: Oct. 25, 2016

(54) LEAD COMPOUND FOR OTOPROTECTION: TARGETING HGF SIGNALING WITH DIHEXA

(71) Applicants: Allison Coffin, Vancouver, WA (US); Joseph Harding, Pullman, WA (US); Leen Kawas, Seattle, WA (US); Phillip Uribe, Vancouver, WA (US)

(72) Inventors: Allison Coffin, Vancouver, WA (US); Joseph Harding, Pullman, WA (US); Leen Kawas, Seattle, WA (US); Phillip Uribe, Vancouver, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 14/720,061

(22) Filed: May 22, 2015

(65) Prior Publication Data

US 2015/0337024 A1 Nov. 26, 2015

Related U.S. Application Data

(60) Provisional application No. 62/002,398, filed on May 23, 2014.

(51) Int. Cl.
*A61K 38/00* (2006.01)
*C07K 16/00* (2006.01)
*C07K 14/475* (2006.01)
*C07K 5/065* (2006.01)
*C07K 5/062* (2006.01)
*C07K 5/072* (2006.01)

(52) U.S. Cl.
CPC ......... *C07K 14/4753* (2013.01); *C07K 5/0606* (2013.01); *C07K 5/06078* (2013.01); *C07K 5/06104* (2013.01); *C07K 5/06113* (2013.01); *A61K 38/00* (2013.01)

(58) Field of Classification Search
None
See application file for complete search history.

(56) References Cited

U.S. PATENT DOCUMENTS 6,235,929 B1 * 5/2001 Powers ................. C07C 271/22
544/168

* cited by examiner

*Primary Examiner* — Jeanette Lieb
(74) *Attorney, Agent, or Firm* — Whitham, Curtis & Cook, P.C.

(57) ABSTRACT

A novel method of preventing or reducing ototoxicity in vertebrates undergoing treatment with therapeutically effective amounts of platinum-based chemotherapeutic agents such as cisplatin or aminoglycoside antibiotics is disclosed herein. The method(s) comprise administering an effective amount of an otoprotective agent comprising Dihexa prior to, concomitantly with, or subsequently to administration of the platinum-based chemotherapeutic agent or aminoglycoside antibiotic.

4 Claims, 5 Drawing Sheets

LEAD COMPOUND FOR OTOPROTECTION: TARGETING HGF SIGNALING WITH DIHEXA

The present application claims under 35 U.S.C. §119, the priority benefit of U.S. Provisional Application No. 62/002,398 filed May 23, 2014, entitled: "A NOVEL LEAD COMPOUND FOR OTOPROTECTION: TARGETING HGF SIGNALING WITH DIHEXA." The disclosure of the foregoing application is incorporated herein by reference in its entirety.

BACKGROUND OF THE INVENTION

1. Field of the Invention

The present invention relates to the field of compounds that protect against ototoxicity and of treating an individual with compounds identified using the present methods herein. More particularly, the present embodiments herein relate to the activation of the hepatocyte growth factor (HGF) via a small molecule drug so as to protect hair cells from ototoxicity.

2. Discussion of the Related Art

Hearing loss afflicts over ten percent of the population of the United States. Hearing in vertebrates depends critically on hair cells, the sensory cells of the organ of Corti in the inner ear. Hearing loss is associated with the loss of such hair cells, which is also often accompanied by deterioration of the spiral ganglion neurons which transduce auditory signals to the brain from the hair cells that transduce sound stimuli into electrical impulses.

In particular, these cells are exquisitely sensitive to sound, and to damage from a variety of sources including excessive noise and specific drugs, called ototoxins, including aminoglycoside antibiotics and platinum-based chemotherapy agents (Schacht et al., 2008). Symptoms of damage due to ototoxicity include partial or profound hearing loss, vertigo and tinnitus. Aminoglycoside antibiotics such as gentamicin and kanamycin are used worldwide due to their high efficacy and low cost and are known to kill hair cells in the mammalian inner ear with dose-dependent sensorineural hearing loss estimated in up to 20% of patients treated with these life-saving antibiotics (Rizzi and Hirose, 2007; Xie et al., 2011). Gentamicin is indispensable for treating bacterial sepsis in neonates (Committee on Infectious et al., 2011; Sivanandan et al., 2011). Kanamycin is essential for treating tuberculosis in sub-Saharan Africa (Fairlie et al., 2011; Falzon et al., 2011), and is the preferred aminoglycoside used for murine in vivo ototoxicity testing (e.g., Wu et al., 2001). Similarly, the chemotherapy agent cisplatin, widely used to treat epithelial tumors, such as ovarian and bladder cancers, causes significant hearing loss in over 20% of patients (Rybak, 2007). As of 2011, approximately 10 million people in the UK suffer from hearing loss, which is often associated with social isolation, depression, and economic losses (Dalton et al., 2003; Action on Hearing Loss, 2011; Helvik et al., 2012). A major gap in the ability to prevent hearing loss is the lack of approved therapeutics that protect hair cells from ototoxic damage.

Hepatocyte growth factor (HGF) is a potent neurotrophin with known roles in cellular migration, proliferation, and protection. Prior research both in cochlear explants and in vivo suggests that HGF is upregulated in response to aminoglycoside treatment and that exogenous HGF may protect hair cells from ototoxic insult (Oshima et al., 2003; Kikkawa et al., 2009). However, exogenously administered HGF is impractical in a clinical setting due to low blood-brain barrier permeability and short half-life.

Accordingly, there is a need for otoprotective compounds to prevent or provide treatment of hearing impairment due to, for example, ototoxic chemicals. In particular, the otoprotective compound provided herein is beneficial in the context of hazards arising from ototoxic chemicals of aminoglycoside antibiotics or platinum-based chemotherapy agents, while substantially preserving the in vivo microcidal or anti-tumor properties of these compounds when administered prior to, concomitantly with, or subsequent to administration of such therapeutic drugs. The present invention addresses such a need.

SUMMARY OF THE INVENTION

The present application is directed to a method of treating or preventing hearing loss a subject in need thereof that includes, administering to said subject one or more hepatocyte growth factor (HGF) mimics having the formula

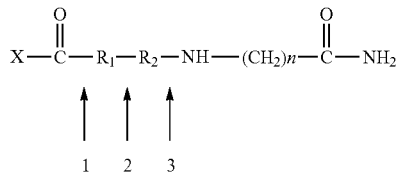

where

X=(CH$_2$)m where m is 3-8, or a substituted or unsubstituted phenyl;

R$_1$ is a D or L cysteine, phenyalanine, aspartic acid, glutamic acid, serine, tyrosine, homocysteine, homoserine or homophenylalanine amino acid residue;

R$_2$ is a D or L isoleucine, leucine or valine amino acid residue; and n ranges from 3-7;

and wherein covalent bonds 1, 2 and 3 are either peptide bonds or reduced peptide bonds.

A second aspect of the present application is directed to a method of protecting from ototoxic and noise induce damage and/or bringing about hair cell replacement in a subject in need thereof that includes: administering to said subject one or more hepatocyte growth factor (HGF) mimics having formula

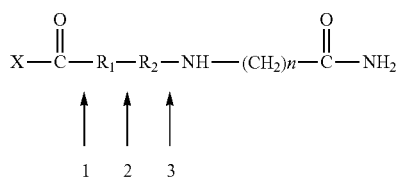

where

X=(CH$_2$)n where m is 3-8, or a substituted or unsubstituted phenyl;

R$_1$ is a D or L cysteine, phenyalanine, aspartic acid, glutamic acid, serine, tyrosine, homocysteine, homoserine or homophenylalanine amino acid residue;

R$_2$ is a D or L isoleucine, leucine or valine amino acid residue; and n ranges from 3-7; and wherein covalent bonds 1, 2 and 3 are either peptide bonds or reduced peptide bonds.

DETAILED DESCRIPTION

Figure 1:
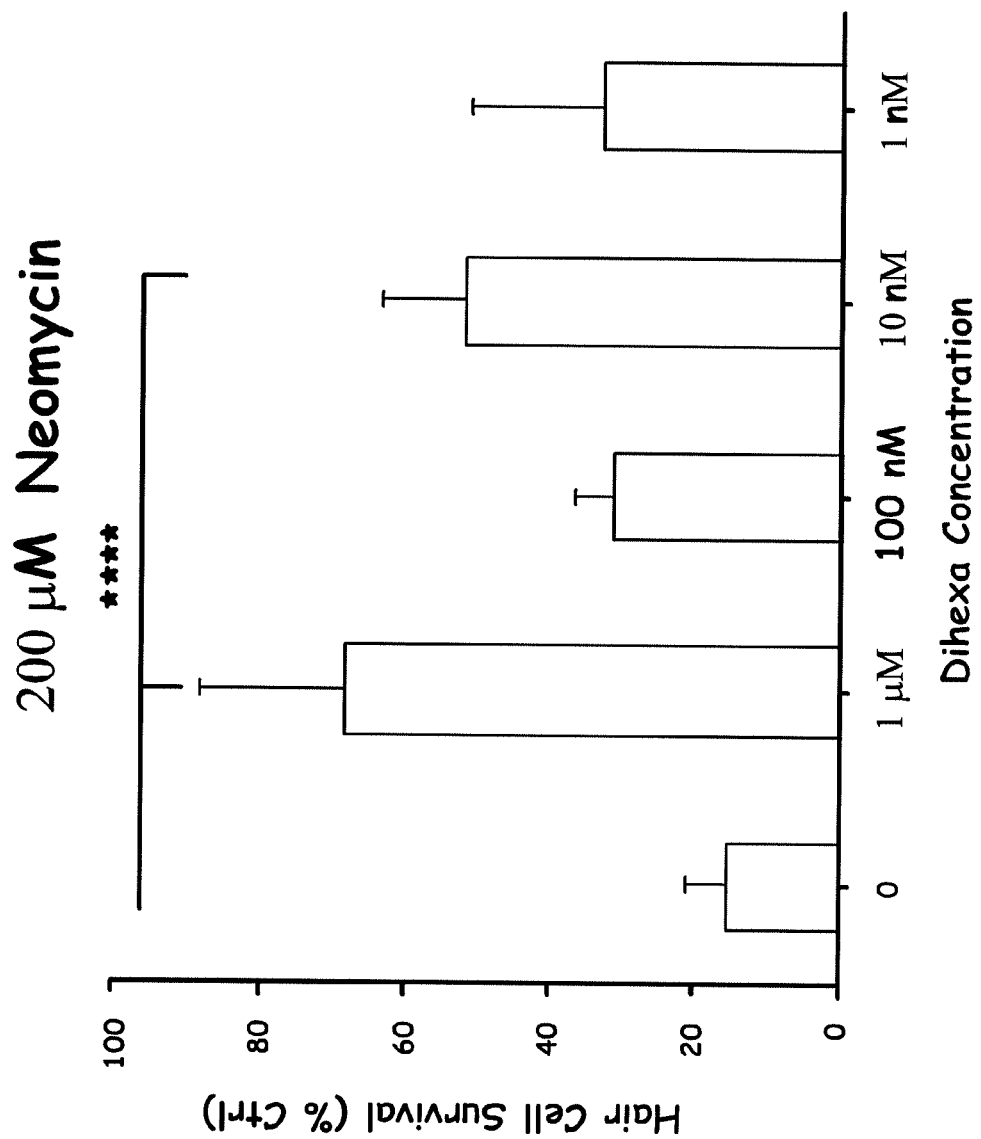
FIG. 1 shows Dihexa concentrations versus hair cell survival percentages with respect to protection against Neomycin-induced hair cell death, N=6-22 fish/treatment, data presented as mean+1 s.d. *p<0.005. **p<0.001.

In the description of the invention herein, it is understood that a word appearing in the singular encompasses its plural counterpart, and a word appearing in the plural encompasses its singular counterpart, unless implicitly or explicitly understood or stated otherwise. Moreover, the terms used herein unless otherwise specified have the meanings commonly understood by those skilled in the art. Furthermore, it is understood that for any given component or embodiment described herein, any of the possible candidates or alternatives listed for that component may generally be used individually or in combination with one another, unless implicitly or explicitly understood or stated otherwise.

Additionally, it is to be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

It is also to be appreciated that the term "ototoxicity," refers to any detrimental or pathologic change in the structure or function of the ear, including changes in hearing and balance. Functional changes can include, but are not limited to, hearing loss or other changes in auditory threshold for any stimulus, perception of sound, ability to identify, localize, recognize, distinguish between, or process sounds, and/or distortion of sounds or any abnormality as measured by conventional auditory tests. This term also includes tinnitus (ringing or noises in the ear), which includes any perception of sound that is not in response to an external signal. Structural changes can include any intra- or extra-cellular, multicellular, or organ change in the auditory or vestibular pathways from the external ear up through and including the cortex and all pathways in between.

General Description

The multifunctional growth factor hepatocyte growth factor (HGF) and its receptor Met are important mediators for mitogenesis, motogenesis, and morphogenesis in a wide range of cell types (Birchmeier et al., 2003) including epithelial (Kakazu et al., 2004), endothelial (Kanda et al., 2006), and hematopoietic cells (Ratajczak et al., 1997), neurons (Thompson et al., 2004), melanocytes (Halaban et al., 1992), and hepatocytes (Borowiak et al., 2004). Furthermore, dysregulation of the HGF/Met system often leads to neoplastic changes and to cancer (in both human and animal) where it contributes to tumor formation, tumor metastasis, and tumor angiogenesis (Christensen et al., 2005; Liu et al., 2008). Over-activation of this signaling system is routinely linked to poor patient prognosis (Liu et al., 2010).

It is to be noted that the main contribution of the embodiments herein is directed to the use of a stable bioavailable synthetic Hepatocyte growth factor (HGF) mimetic, i.e., Dihexa, that can be orally administered and that readily traverses the blood-brain barrier analogous to the blood-labyrinth barrier that protects the inner ear. Such a synthetic HGF mimetic forms a functional ligand by dimerizing with endogenous HGF to activate the HGF receptor and downstream signals. In conditional HGF knockout mice, cochlear outer hair cells degenerate, implicating HGF in hair cell maintenance and suggesting that basal HGF expression is required in the inner ear (Schultz et al., 2009).

Information with respect to Hepatocyte growth factor (HGF) mimetics can be found in U.S. Pat. No. 8,598,118, entitled "Hepatocyte growth factor Mimics As Therapeutic Agents," to Harding et al., and assigned to the Assignees of the present application provides details with respect to HGF mimetics, to include Dihexa, and is incorporated herein in its entirety.

With respect to Dihexa in particular, in vivo Dihexa administration significantly attenuates symptoms in rat dementia and Parkinson's Disease models. The present example methodologies capitalize on this suggested aspect by providing Dihexa to exert general protective and restorative activity in mammalian neurodegenerative conditions (McCoy et al., 2013; unpublished data). Dihexa's regenerative activity is expected since activation of its molecular target, HGF, has been shown to possess neuroprotective/neurorestorative activity related to amyotrophic lateral sclerosis (Kadoyama et al., 2007), Parkinson's disease (Koike et al., 2006; Lan et al., 2008), spinal cord trauma (Kitamura et al., 2011), and multiple sclerosis (Bai et al., 2011). As such, HGF/c-Met system is specifically designed to respond to nervous system injury by activating protective and restorative processes. This is further supported by the elevation of HGF in the central nervous system that is apparent in many neurodegenerative and neurotraumatic disorders (Shimamura et al., 2007; Kato et al., 2003; Salehi and Rajaei 2010; Muller et al., 2012). Ongoing studies with wound repair, retinal degeneration, and the CNS response to *Arboviral encephalitides*, like West Nile, further validate the regenerative impact of Dihexa.

Short duration safety studies with Dihexa have uncovered no apparent toxicity. Of particular note is a lack of neoplastic induction, since c-Met is recognized as an oncogene. This is unsurprising since oncogenesis requires multiple mutations including both oncogene induction and tumor suppressor attenuation. Accordingly, Dihexa, as utilized herein, can also be delivered locally via intratympanic membrane injection of a Dihexa-containing hydrogel (e.g., Salt et al., 2011; Wang et al., 2011) as a way of the proof-of-principle that Dihexa is robustly otoprotective in for example, but not limited to, pre-clinical models.

The otoprotective capabilities of Dihexa is demonstrated herein in a zebrafish system, and in a rodent ototoxicity model, both in vitro and in vivo. Zebrafish, historically, is a desirably animal because certain organs can be studied optically because of its transparent body. Further, in a comparison to humans, Zebrafish has an 80% homology in terms of the full genome sequence, is almost the same in terms of the number of genes, and is very similar also in terms of the development and structure of principal organs and tissues. Therefore, the auditory toxicity of a chemical substance screened by using Zebrafish as a model animal is highly likely to be applicable to a human.

Specifically, Zebrafish has organs present on the skin surface called lateral line organs, which are clusters of sensory hair cells that beneficially provide for a tractable in vivo model for ototoxicity and protection studies (Coffin et al., 2009, 2010, 2013). Specifically and as alluded to above, such lateral line hair cells are functionally and structurally similar to mammalian inner ear hair cells as both show similar responses to toxins, including aminoglycoside antibiotics and cisplatin (Harris et al., 2003; Ou et al., 2007; Coffin et al., 2010). A previous study of aminoglycoside toxicity in the lateral line uncovered a novel protective agent, PROTO-1, which also confers protection from aminoglycosides in vivo in rats, demonstrating that compounds first identified in zebrafish offer translational potential in mammals (Owens et al., 2008, Rubel et al., 2011).

Accordingly, while the benefits of Dihexa is primarily demonstrated herein in a model using Zebrafish and/or rodents, the basis of the present application is directed to methods of administering an effective amount of an otoprotective agent comprising Dihexa prior to, concomitantly with, or subsequently to administration of, for example, platinum-based chemotherapeutic agents or aminoglycoside antibiotics so as to activate the hepatocyte growth factor (HGF) and protect hair cells from ototoxicity, the results of which beneficially prevents hearing loss in mammals, such as humans.

Specific Description

Peptide analogs or mimics of HGF (also referred to as "growth factor mimics" or "analogs") having a variety of therapeutic utilities have the following general structural formula:

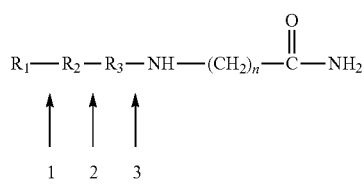

where $R_1$ is an N-acyl group such as, for example, hexanoyl, heptanoyl, pentanoyl, butanoyl, propanoyl, acetanoyl, or benzoyl, a substituted or unsubstituted phenyl, a D or L norleucine, an amino acid (D or L) such as, for example, lysine, arginine, norvaline, ornithine, or S-benzyl cysteine amino acid residues;

$R_2$ is an amino acid (D or L), such as, for example, tyrosine, cysteine, phenyalanine, aspartic acid, glutamic acid, glycine, tryptophan, lysine, homocysteine, homoserine, homophenylalanine;

$R_3$ is a D or L isoleucine, leucine or valine amino acid residue; and n ranges from 3-6;

and wherein covalent bonds 1, 2 and 3 are either peptide bonds (e.g. —CO—NH— or reduced peptide bonds ($CH_2$—$NH_2$).

An exemplary peptide bond and reduced peptide bond are depicted below:

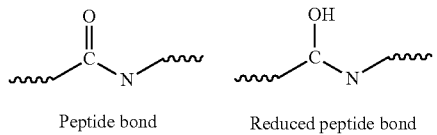

Peptide bond      Reduced peptide bond

The present invention will be more fully understood by reference to the following examples of 1) determining the extent to which Dihexa protects zebrafish hair cells from ototoxins; 2) determining the degree to which downstream targets in the HGF signaling cascade are required for Dihexa-mediated hair cell protection; 3) evaluating the otoprotective capacity of Dihexa; and 4) verifying the relevant doses of Dihexa so as to not interfere with the bactericidal properties of aminoglycosides or the tumoritoxicity of cisplatin, all of which are intended to be illustrative of the example embodiments of the present invention, but not limiting thereof.

Extent to which Dihexa Protects Zebrafish Hair Cells from Ototoxins

Figure 2:
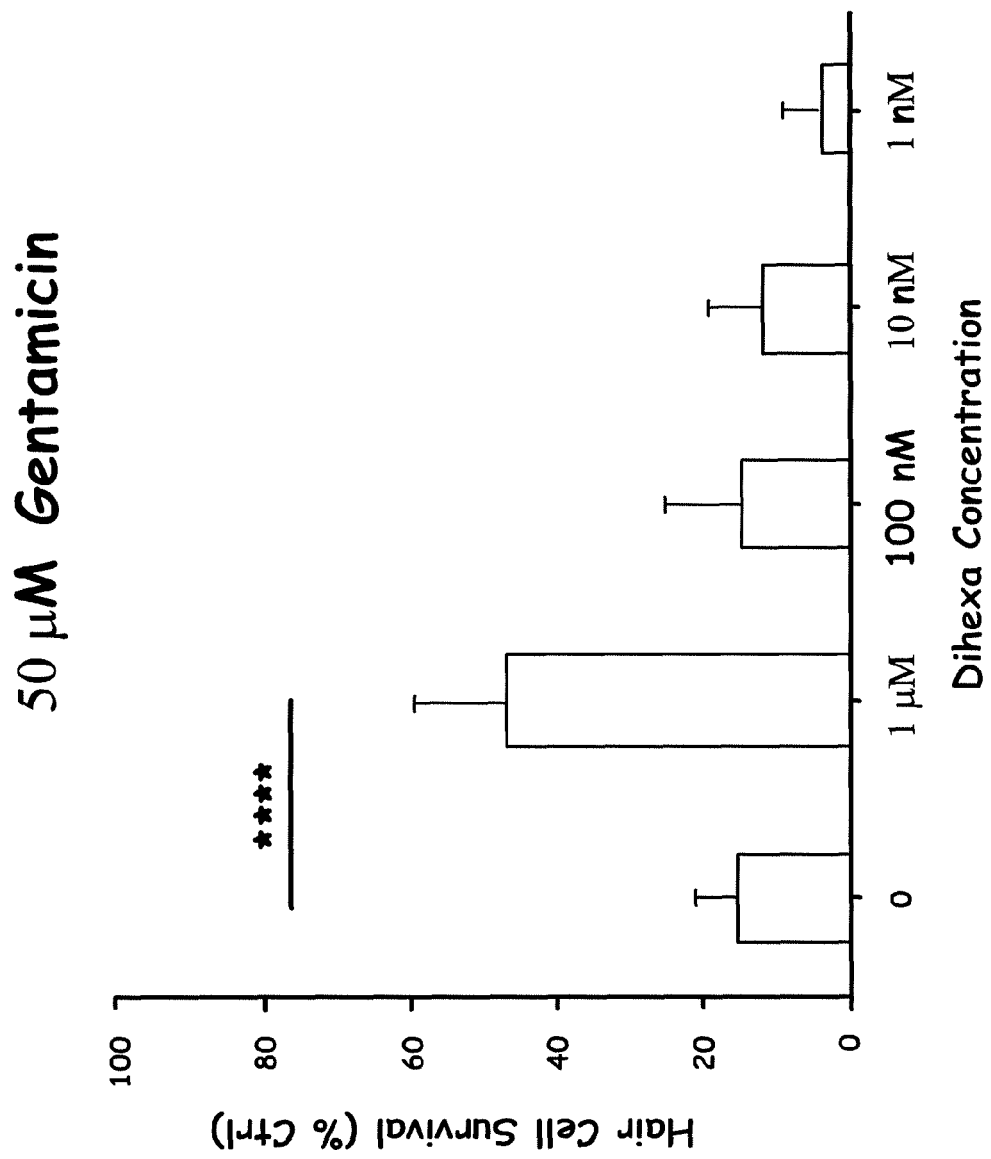
FIG. 2 shows Dihexa concentrations versus hair cell survival percentages to protection against Gentamycin-induced hair cell death, N=6-22 fish/treatment, data presented as mean+1 s.d. *p<0.005. **p<0.001.

Turning now to the drawing, FIG. 1 and FIG. 2 show example dose effects using Dihexa that demonstrate the protection of zebrafish lateral line hair cells from aminoglycoside toxicity. In particular, FIG. 1 shows hair cell protection from 200 µM Neomycin toxicity levels while FIG. 2 shows hair cell protection from 50 µM Gentamycin gentamicin toxicity levels. The data is presented as mean+1 standard deviation (s.d.) *p<0.005. **p<0.001, with the number of stars being the confidence for the measurements and the p (i.e., p-value) being the probability of obtaining a test statistic result at least as extreme as the one that was actually observed. It is to be appreciated the differences are considered significant at P<0.05. Note also that the 0 Dihexa concentration levels in FIG. 1 and FIG. 2 are control levels no protective Dihexa was introduced as just Neomycin and Gentamicin is present in the hair cells. It is to be appreciated FIG. 1 and in FIG. 2 demonstrates that substantially all the Dihexa dose concentrations provide surprisingly appreciable and beneficial levels of hair cell protection against the introduced aminoglycosides with the 1 µM dose levels of Dihexa showing the most promising results with hair cell survival rates at respectively greater than 60%, as shown in FIG. 1 and greater than 40%, as shown in FIG. 2.

It is to be noted that while the protective effects with respect to aminoglycoside damage is shown in FIG. 1 and FIG. 2, such a demonstrated ability can also be shown by the methods herein with respect to Dihexa protection against a variety of other ototoxic agents, such as, but not limited to, cisplatin-induced toxicity. Such an example method of operation can be enabled by providing Dihexa concentrations for each ototoxin. In particular, Larval zebrafish, often 5-6 days old, can be pre-treated with variable concentrations of Dihexa for 1 hr (e.g., a concentration range of 1 nM up to about 10 µM), then incubated with Dihexa in the presence of either 200 µM neomycin (1 hr), 100 µM gentamicin (6 hrs), 400 µM kanamycin (6 hrs), 500 µM cisplatin (6 hrs), or Dihexa only (6 hrs). Toxin concentrations and treatment times are selected so that in each case, a range of about 60% up to about 80% hair cell loss is achieved, sufficient to robustly detect protection. While the methodology described above provides desirable information for a variety of ototoxins, the Dihexa-mediated protection for neomycin, gentamicin, and kanamycin, as enabled herein, is the most desirable because these three antibiotics activate partially independent cell death pathways, such that a single compound may not universally protect hair cells from aminoglycoside toxicity (Owens et al., 2009; Coffin et al., 2009; Vlasits et al., 2012; Coffin et al., 2013).

As part of the analysis process, after treatment, hair cell survival is more often quantitatively assessed by labeling with either the vital dye DASPEI for assessment in live, anesthetized fish, or with an antibody to parvalbumin for quantification in fixed tissue (Harris et al., 2003; Owens et al., 2009; Coffin et al., 2009, 2013). DASPEI allows for rapid assessment with minimal tissue processing time, while immunofluorescence is used to validate DASPEI assessment scores. Labeled hair cells are thereafter viewed using fluorescence microscopy and quantified as described in the published literature (e.g., Harris et al., 2003; Coffin et al., 2009, 2013).

As another example method step of operation, after an optimally protective Dihexa concentration is determined, a second series of dose-response analyses can be utilized to determine the degree to which Dihexa protects against a range of ototoxin concentrations. As a beneficial example, the Dihexa concentration can be held constant and the toxin (e.g., a range of 0 up to about 400 µM for neomycin or gentamicin, a range of 0-1000 µM for kanamycin and cisplatin) with the hair cells assessed as described herein.

Figure 3:
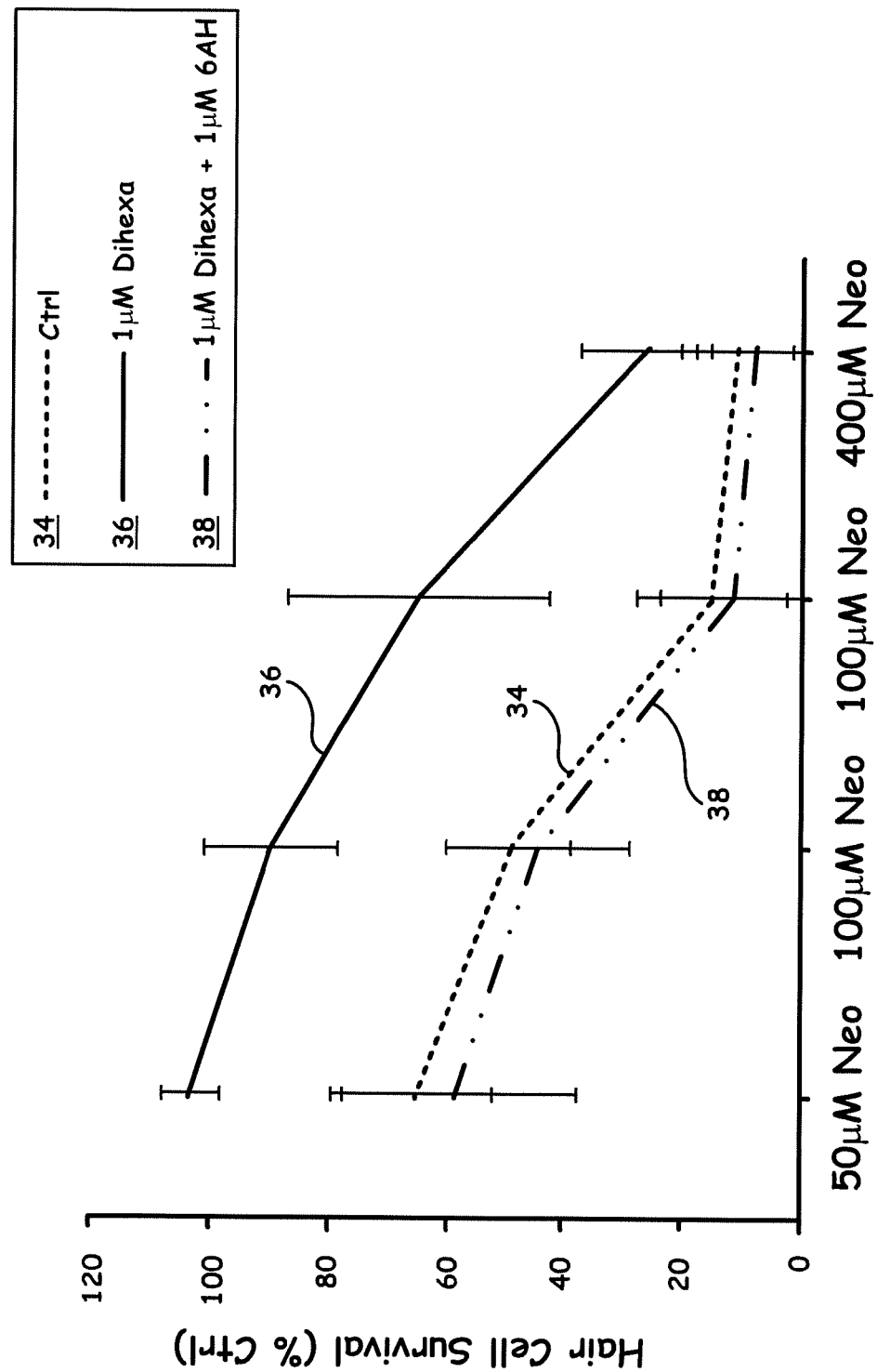
FIG. 3 shows 1 μM Dihexa protection from Neomycin-induced hair cell death as compared to the same Dihexa dose response attenuated with concurrent exposure to the Hepatocyte growth factor (HGF) antagonist 6AH, N=6-9 animals/treatment, data presented as mean±1 s.d. ****p<0.001.
Figure 4:
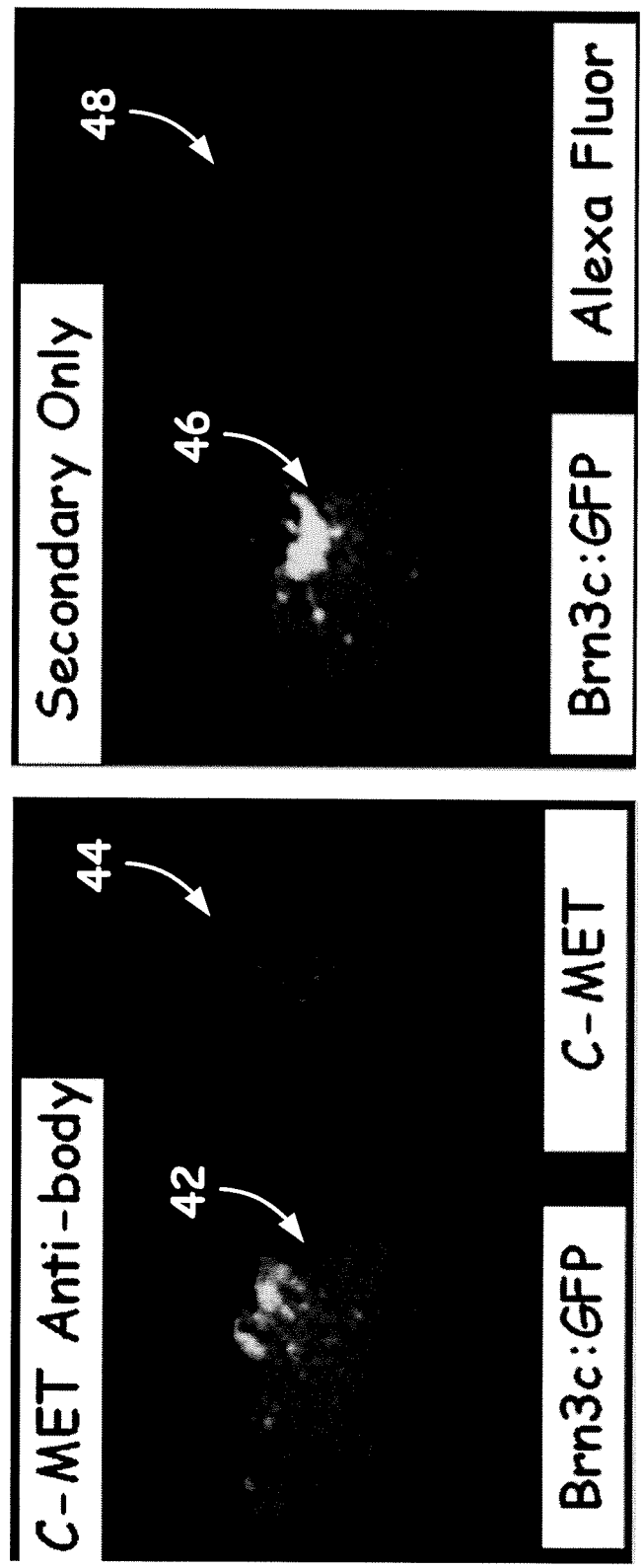
FIG. 4A shows C-met localizing to lateral line hair cells in a transgenic fish line that expressed membrane-bound Green Fluorescent Protein (GFP) in hair cells (Brn3c:GFP).
FIG. 4B illustrates the Alexa Fluorphore operating without the primary antibody, as shown in FIG. 4A.
Figure 5:
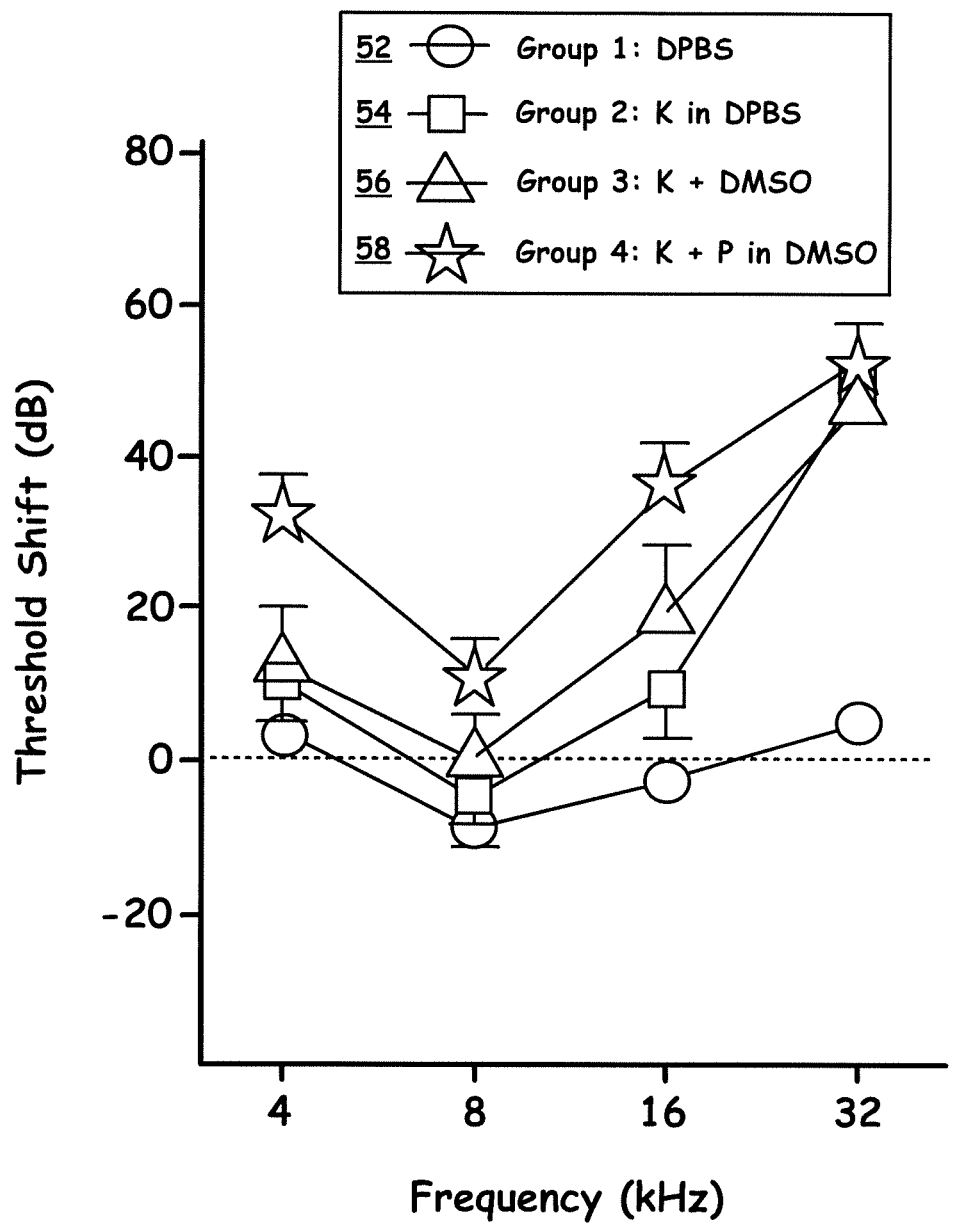
FIG. 5 shows details of model depicting whether individual compounds increase or decrease the degree of ototoxicity.

Degree to which Downstream Targets in the HGF Signaling Cascade are Required for Dihexa-Mediated Hair Cell Protection FIG. 3 shows Dihexa conferring robust protection from Neomycin-induced hair cell death, wherein this protection is attenuated with concurrent exposure to the HGF antagonist 6AH with the data samples (N) being N=6-9 animals/treatment and the data being presented as mean±1 standard deviation (s.d.) ****p<0.001. The data in FIG. 3 provides insight into investigating and understanding the mechanism of Dihexa-mediated protection using pharmacologic and genetic manipulation of HGF signaling. In general, FIG. 3 shows dose response and the correlated hair cell survivability as a user adds Neomycin. In particular, FIG. 3 shows a control sample 34 (also denoted with a dashed line) with only levels of Neomycin and no Dihexa provided. However, note in FIG. 3 that as 1 µM of Dihexa is introduced, the hair survivability along the denoted Neomycin dose levels beneficially increases (i.e., plot 36 as also denoted by a solid line). By contrast, FIG. 3 also shows a plot of the hair survivability along the denoted Neomycin dose levels decreasing (see Ref character 38 as also denoted with the dotted and dashed plot line) due to being attenuated with concurrent exposure to the HGF antagonist 6AH. It is to be noted that the control sample 34 and the attenuated plot 38 due to concurrent exposure to the HGF antagonist 6AH are indistinguishable statistically, as illustrated by the provided error bars in FIG. 3.

the natural polymer-derived macromonomer 10 is prepared, by introducing polymerizable unsaturated cross-linkable units 18 onto the natural polymer backbone 14 so as to modify the natural polymer itself by the reaction with predetermined chemical compounds. For example, suitable chemicals to introduce such cross-linkable units 18 to the macromonomers include, but are not limited to, methacrylic anhydride, and maleic anhydride. As an example alternative, the natural polymer is pre-treated before turned into the macromonomer 10, e.g., the natural polymer is hydrolyzed. The natural polymer-derived macromonomer product can then be used directly in aqueous solution or be used after proper methods of drying.

The present invention will be more fully understood by reference to the following examples, which are intended to be illustrative of the present invention, but not limiting thereof.

EXAMPLES

Measurement of Swelling

The swelling of the superabsorbent polymer materials is evaluated by comparing the weight of the swollen gel to that of the dry gel and denoted as Q. The swelling ratio based on weight, Q, is determined according to the following formula:

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A method of treating or preventing hearing loss a subject in need thereof, comprising:
   administering to said subject one or more hepatocyte growth factor (HGF) mimics having formula

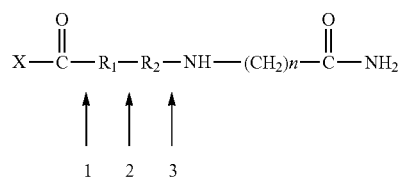

where
   $X=(CH_2)m$ where m is 3-8, or a substituted or unsubstituted phenyl;
   $R_1$ is a D or L cysteine, phenyalanine, aspartic acid, glutamic acid, serine, tyrosine, homocysteine, homoserine or homophenylalanine amino acid residue;
   $R_2$ is a D or L isoleucine, leucine or valine amino acid residue; and
   n ranges from 3-7;
and wherein covalent bonds 1, 2 and 3 are either peptide bonds or reduced peptide bonds.

2. The method of claim 1, wherein said HGF mimic is hexanoic-tyrosine-isoleucine-(6)-amino-hexanoic amide.

3. A method of protecting from ototoxic and noise induce damage and/or bringing about hair cell replacement in a subject in need thereof, comprising:
   administering to said subject one or more hepatocyte growth factor (HGF) mimics having formula

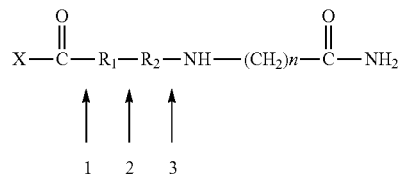

where
- X=(CH$_2$)n where m is 3-8, or a substituted or unsubstituted phenyl;
- R$_1$ is a D or L cysteine, phenyalanine, aspartic acid, glutamic acid, serine, tyrosine, homocysteine, homoserine or homophenylalanine amino acid residue;
- R$_2$ is a D or L isoleucine, leucine or valine amino acid residue; and
- n ranges from 3-7;

and wherein covalent bonds 1, 2 and 3 are either peptide bonds or reduced peptide bonds.

4. The method of claim 3, wherein said HGF mimic is hexanoic-tyrosine-isoleucine-(6) amino hexanoic amide.

* * * * *